(12) United States Patent
Roy et al.

(10) Patent No.: US 9,585,587 B2
(45) Date of Patent: Mar. 7, 2017

(54) FIXED LOOP DEFLECTABLE ELECTROPHYSIOLOGY CATHETERS HAVING AN EXTENDED BRAID PRIMARY SHAFT COUPLED TO THE PERIPHERY OF THE FIXED LOOP AND METHODS OF MANUFACTURING THEREFOR

(75) Inventors: Pianka Roy, Irvine, CA (US); Alan de la Rama, Cerritos, CA (US); Jennifer Velasco, Orange, CA (US)

(73) Assignee: St. Judge Medical, Atrial Fibrillation Division, Inc., St. Paul, MN (US)

( * ) Notice: Subject to any disclaimer, the term of this patent is extended or adjusted under 35 U.S.C. 154(b) by 18 days.

(21) Appl. No.: 12/982,629

(22) Filed: Dec. 30, 2010

(65) Prior Publication Data

US 2012/0116200 A1    May 10, 2012

Related U.S. Application Data

(60) Provisional application No. 61/411,694, filed on Nov. 9, 2010.

(51) Int. Cl.
*A61B 18/18* (2006.01)
*A61B 5/042* (2006.01)
(Continued)

(52) U.S. Cl.
CPC .......... *A61B 5/0422* (2013.01); *A61B 5/6856* (2013.01); *A61B 18/1492* (2013.01);
(Continued)

(58) Field of Classification Search
CPC ............ A61B 5/0422; A61M 25/0147; A61M 25/0136; A61M 25/0144; A61M 2025/0161; A61M 25/0133
(Continued)

(56) References Cited

U.S. PATENT DOCUMENTS 5,263,493 A   11/1993   Avitall
5,628,313 A    5/1997   Webster, Jr.
(Continued)

FOREIGN PATENT DOCUMENTS

JP    2005-505328    2/2005
JP    2007-518494    7/2007
(Continued)

OTHER PUBLICATIONS

"International Search Report & Written Opinion", PCT/US2011/059922 Feb. 22, 2012.
(Continued)

*Primary Examiner* — Joseph Stoklosa
*Assistant Examiner* — Brian M Antiskay
(74) *Attorney, Agent, or Firm* — Dykema Gossett PLLC (57) ABSTRACT

An EP catheter includes a tubular body having a proximal region, a neck region, and a distal portion predisposed into a single shallow helical fixed-diameter loop configuration and including a plurality of diagnostic electrodes. In deflectable catheter forms, at least one activation wire extends through at least a portion of the proximal region of the catheter body and is adapted to deflect the up to approximately 180 degrees relative to the proximal region. The catheter can be operated manually by a clinician or via a clinician-surrogate such as a computer processor-controlled surgical system. In addition, a variety of localization, visualization, and/or orientation-specific elements can be incorporated into the devices described, depicted, and claimed herein (e.g., metallic coil members, active impedance emitting or receiving electrodes, fluoroscopically opaque materials, and the like).

20 Claims, 9 Drawing Sheets

(51) Int. Cl.
*A61B 5/00* (2006.01)
*A61B 18/14* (2006.01)
*B23K 1/00* (2006.01)
*A61B 5/04* (2006.01)
*A61B 17/00* (2006.01)
*A61B 18/00* (2006.01)

(52) U.S. Cl.
CPC ...... *B23K 1/0008* (2013.01); *A61B 2017/003* (2013.01); *A61B 2017/00323* (2013.01); *A61B 2017/00867* (2013.01); *A61B 2018/0016* (2013.01); *A61B 2018/00214* (2013.01); *A61B 2018/00351* (2013.01); *A61B 2018/1435* (2013.01); *A61B 2562/0209* (2013.01)

(58) Field of Classification Search
USPC ........ 600/373–374, 381, 466, 508–509, 585; 606/32–38, 41–42, 45; 607/115–116, 607/119, 122–123, 131
See application file for complete search history.

(56) References Cited

U.S. PATENT DOCUMENTS

| | | | |
|---|---|---|---|
| 5,680,860 | A | 10/1997 | Imran |
| 6,106,522 | A * | 8/2000 | Fleischman et al. ............ 606/41 |
| 6,254,568 | B1 | 7/2001 | Ponzi |
| 6,577,902 | B1 | 6/2003 | Laufer et al. |
| 6,613,046 | B1 * | 9/2003 | Jenkins et al. ................. 606/41 |
| 7,377,906 | B2 | 5/2008 | Selkee |
| 7,706,891 | B2 | 4/2010 | Hastings et al. |
| 7,789,877 | B2 | 9/2010 | Vanney |
| 2001/0007070 | A1 | 7/2001 | Stewart et al. |
| 2002/0022839 | A1 | 2/2002 | Stewart et al. |
| 2002/0177765 | A1 * | 11/2002 | Bowe et al. ................... 600/374 |
| 2003/0088244 | A1 | 5/2003 | Swanson et al. |
| 2004/0147827 | A1 | 7/2004 | Bowe |
| 2005/0187455 | A1 | 8/2005 | Rashidi |
| 2006/0241366 | A1 * | 10/2006 | Falwell et al. ................. 600/374 |
| 2006/0247613 | A1 | 11/2006 | White |
| 2007/0270679 | A1 | 11/2007 | Nguyen et al. |
| 2008/0161774 | A1 | 7/2008 | Hastings et al. |
| 2008/0234661 | A1 * | 9/2008 | Hastings et al. .............. 604/528 |
| 2009/0032789 | A1 | 2/2009 | Kennedy et al. |
| 2009/0062789 | A1 | 3/2009 | Rioux et al. |
| 2009/0163794 | A1 | 6/2009 | Muranushi et al. |
| 2009/0287210 | A1 * | 11/2009 | Kauphusman et al. ........ 606/41 |
| 2010/0030114 | A1 | 2/2010 | Nguyen et al. |
| 2010/0069733 | A1 | 3/2010 | Kastelein et al. |
| 2010/0168676 | A1 * | 7/2010 | Datta et al. ................... 604/171 |
| 2010/0168827 | A1 | 7/2010 | Schultz |
| 2010/0249568 | A1 * | 9/2010 | Stehr et al. ................... 600/374 |

FOREIGN PATENT DOCUMENTS

| | | |
|---|---|---|
| JP | 2010-507403 | 3/2010 |
| WO | 95/10318 A1 | 4/1995 |
| WO | 03/030713 A2 | 4/2003 |
| WO | 2005/070491 A2 | 8/2005 |
| WO | 2006044794 A2 | 4/2006 |
| WO | 2008/049084 A2 | 4/2008 |
| WO | 2010048676 A1 | 5/2010 |

OTHER PUBLICATIONS

Atrial Fibrillation Catalog Excerpt, pp. 53-54, Jul. 2007.
Atrial Fibrillation Electrophysiology U.S. Catalog Excerpt, pp. 122-124, St. Jude Medical, 2010.
Jean-Paul Albenque et al, "Atrial Fibrillation Electroanatomical 3D Mapping Optimisation Thanks to a Novel High-density Mapping Catheter—The Inquire AFocus II" Touch Briefings, pp. 63-65, Sep. 2010.
News Release, "St. Jude Medical Showcases Latest Products at Boston Atrial Fibrillation Symposium 2010", Jan. 2010.
"Inquiry AFocus II EB Catheter, Smallest Turning Radius of Any Circular Mapping Catheter", St. Jude Medical, 2010.
"Inquiry AFocusII, Single-Catheter Solution for Streamlined Diagnostics and Mapping", St. Jude Medical, 2009.

* cited by examiner

FIXED LOOP DEFLECTABLE ELECTROPHYSIOLOGY CATHETERS HAVING AN EXTENDED BRAID PRIMARY SHAFT COUPLED TO THE PERIPHERY OF THE FIXED LOOP AND METHODS OF MANUFACTURING THEREFOR

STATEMENT OF INCORPORATION BY REFERENCE

This non-provisional U.S. patent application claims the benefit of and priority to provisional U.S. patent application No. 61/411,694 filed 9 Nov. 2010 (the '694 application) relates to U.S. patent application Ser. No. 12/760,337 filed 14 Apr. 2010 (the '337 application). The entire contents of the '694 and the '337 applications are hereby incorporated as if fully set forth herein.

BACKGROUND OF THE INVENTION a. Field of the Invention

The disclosure relates to electrophysiology (EP) catheters for use in medical procedures. In particular, the disclosure relates to a family of catheters for use in diagnostic and therapeutic procedures in and around a patient's cardiac anatomy, such as the ostium of a pulmonary vein.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical EP catheter includes an elongate shaft and one or more electrodes on the distal end of the shaft. The electrodes can be used for diagnostic mapping, or ablation the like. Oftentimes, these electrodes are ring electrodes that extend about the entire circumference of the catheter shaft.

One specific use of an EP catheter is to map the atrial regions of the heart, and in particular the pulmonary veins, which are often origination points or foci of atrial fibrillation. Such EP mapping catheters typically have at least a partial loop shape at their distal end in order to surround the pulmonary vein ostia.

BRIEF SUMMARY OF THE INVENTION

Accordingly, it is the present disclosure relates to a family of EP catheters having highly enhanced deflection capability to effectively access a particular subject's individual anatomy while at the same time rapidly collecting EP diagnostic data from said subject with a distal portion with an offset shaft-to-loop axis (or junction) and having a single shallow helical fixed-diameter loop.

Another embodiment described and depicted herein relates to EP catheters that allow the single shallow helical fixed-diameter loop at the distal end to deflect 180 degrees relative to the remainder of the catheter body in an incredibly small space (e.g., on the order of 50 mm), which is ideal for performing cardiac diagnostic mapping of the atria, for example. In an embodiment, the single shallow helical fixed-diameter loop has an outer-loop diameter of between about 15 mm and about 25 mm, although other dimensions are not excluded. The outer diameter of the catheter body (expressed in units known as French abbreviated as 4 F, for example, each unit of which equals ⅓ of a millimeter, or mm) can vary. For example a majority of the catheter body, the proximal portion, can be on the order of about 7 F and an adjacent neck region can include structure, including an anchoring location for an activation wire, transitions the outer diameter to about 4 F such that the single shallow helical fixed-diameter loop distal portion is 4 F or other uniform outer diameter throughout.

In some embodiments, the single shallow helical fixed-diameter loop distal portion includes 20 electrodes, including a relatively longer distal tip electrode (e.g., 19 discrete 1 mm wide ring-type electrodes and a single 2 mm long distal tip electrode). In one form, 20 electrodes are distributed in a paired bi-polar mapping configuration wherein each pair is equally separated from each other pair (e.g., 2.5 mm apart) and each individual pair is closely situated (e.g., 1 mm apart—including the tip electrode to the most-distal ring-type electrode). Such closely spaced bi-polar pairs tend to reduce so-called far field effects in an in-chamber electrocardiogram (EGM) signal. In another form, 10 discrete electrodes (9 ring-type electrodes and one tip electrode) couple to the single shallow helical fixed-diameter loop distal portion to sense EGM signals and are typically evenly-spaced (e.g., 3 mm, 4 mm, 5 mm, 7 mm, or the like) although that is not a requirement as they may be paired in bi-polar pairs as described above. That is, a 1 mm spacing could be following by a 7 mm spacing (in what can be referred to as a 1-7-1 arrangement). In this form the initial spacing between a tip electrode and the next ring-type electrode might be a different value, for example, 2 mm or some other value.

Accordingly, this disclosure describes EP catheters including: a tubular catheter body having a proximal region, a neck region, and a distal portion predisposed into a single shallow helical fixed-diameter loop distal portion; a plurality of electrodes disposed on the distal portion (e.g., as noted above, 10 or 20—or more or less—also known as deca- and duo-deca pole or polar electrode arrangement—with unipolar and bipolar pairing provided via suitable switching, as desired); a handle joined to the proximal region (for deflecting the distal part of the shaft portion); and a first activation wire extending through at least a portion of the proximal region of the catheter body.

The activation wire deflects the neck region of the catheter body in a common plane. Alternatively, they can deflect the proximal region, the neck region, and/or the looped-portion of the catheter body in different planes. In general, the activation wire couples to a first element (e.g., a round or flat wire, a thread of fiber such as Kevlar, or the like) such that forces are transferred to the shaft proximal of the loop (or the neck portion) via a deflection mechanism such as a rotary knob or a push-pull handle as is known in the EP art.

In yet another aspect, the present invention provides a method of manufacturing an EP catheter. The method generally includes the steps of: joining a proximal portion of a shaft portion of an EP catheter to a deflection mechanism and a distal portion to a proximal region of a peripheral edge (or off-axis arrangement) of a distal single shallow helical fixed-diameter loop region having a plurality of electrodes disposed thereon; joining the deflection mechanism to a wire coupled to a distal portion of a segment of flat wire near the neck region and passing through a lubricious tube fastened to the segment of flat wire (thus the flat wire serving as an anchor structure adapted to deflect the neck region of the EP catheter in a planar manner). A method of delivering therapy via a catheter manufactured according to the foregoing includes: introducing the EP catheter into a patient's body proximate an ostium of interest; actuating the deflection mechanism to deflect the proximal region of the catheter in order to deflect the neck region of the catheter, and advancing or otherwise deploying the single shallow helical fixed-diameter loop portion relative to the ostium of interest.

An advantage of EP catheters designed, built, and implemented according to the present disclosure is that the distal portion thereof (the single shallow helical fixed-diameter loop portion) can be efficiently deflected relative to the remainder of the catheter body and thus can efficiently map various surfaces of a heart via the 10 or 20 (or other number) of electrodes.

Thus, an EP catheter according to this disclosure includes a tubular catheter body having a proximal region, a neck region, and a distal portion predisposed into an single shallow helical fixed-diameter loop configuration and including mapping electrodes arranged in diverse spacings therebetween. In deflectable embodiments, at least one activation wire extends through at least a portion of the proximal region of the catheter body and is adapted to deflect the distal portion (e.g., approximately 180 degrees) relative to the proximal region. The catheter can be operated manually by a clinician or via a clinician-surrogate such as a computer processor-controlled surgical system. In addition, a variety of localization, visualization, and/or orientation-specific elements can be incorporated into the proximal region, neck region, and proximal portion (e.g., metallic coil members, active impedance emitting or receiving electrodes, fluoroscopically opaque materials, and the like) for use in conjunction with an electroanatomical system, for example.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2B' is an enlarged isometric fragmented view of the interior details of the ends of the various connecting elements within the interior of the catheter body of FIG. 2A.

FIG. 2C' is a plan view of a polymer (PEEK) tube having a flattened end to promote adhesive effectiveness at its proximal end to a flat wire (deflection) subassembly that is used to contain a segment of nitinol shape memory wire that forms the single shallow helical fixed-diameter loop distal end of the present family of EP catheters.

DETAILED DESCRIPTION OF THE INVENTION

The present invention will be described with reference to an EP catheter utilized in cardiac EP studies, such as the AFocus II EB diagnostic catheter of St. Jude Medical, Atrial Fibrillation Division, Inc., which can provide access to difficult-to-reach portions of atrial anatomy, in particular the right superior and inferior pulmonary veins. The catheter described, depicted and claimed herein also provides relatively faster cardiac activity data collection (especially in duodecapolar configurations) by rapidly providing the necessary detail to efficiently diagnose complex cardiac arrhythmias. It should be understood, however, that the present teachings can be applied to good advantage in other contexts as well, such as radiofrequency (RF) ablation catheters or other diagnostic cardiac catheters.

Figure 1A:
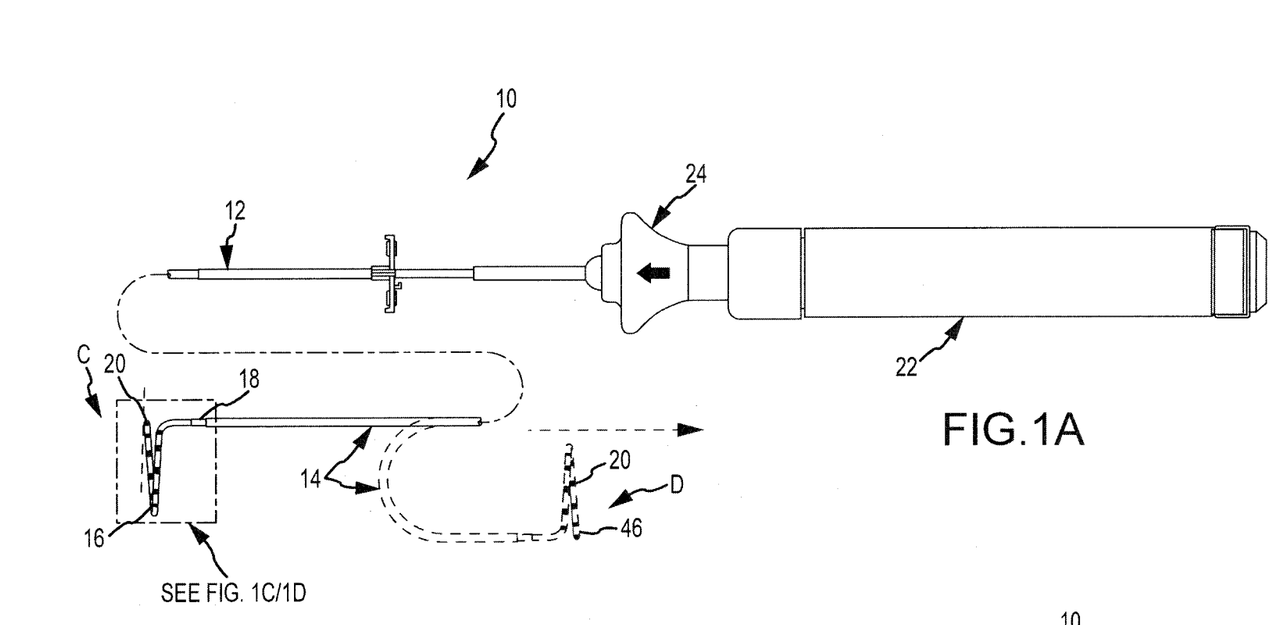
FIG. 1A is a plan view including a partially exploded depiction of an exemplary EP catheter having a distal single shallow helical fixed-diameter loop cardiac mapping portion with EP electrodes disposed in a preconfigured manner, with the partially exploded depiction illustrating the catheter in both a deflected and an undeflected configuration.
Figure 1B:
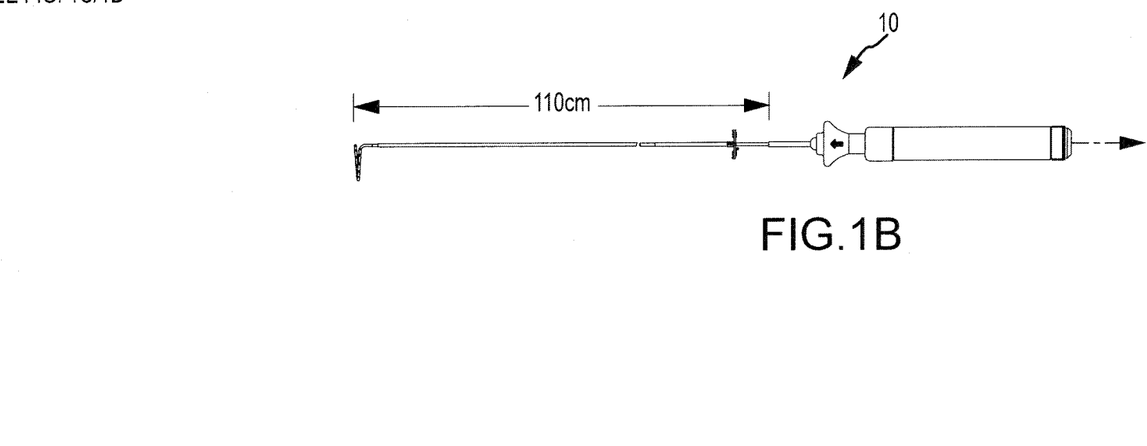
FIG. 1B is a plan view of the exemplary EP catheter illustrated in FIG. 1A in an undeflected configuration.

Referring now to the drawings, FIGS. 1A and 1B depict an EP catheter 10 according to a first aspect of the present invention.

FIG. 1A is a plan view including a partially exploded depiction of an exemplary EP catheter 10 having a distal single shallow helical fixed-diameter loop cardiac mapping portion 16 with EP diagnostic, or mapping, electrodes 20 (as depicted herein arranged in an exemplary decapolar configuration), with the partially exploded depiction illustrating the catheter 10 in both a undeflected and a deflected configuration (denoted as "C" and "D" respectively). The off-axis, or peripheral, junction of the single shallow helical fixed-diameter loop to the neck region of the catheter allows 180 degree deflection in on the order of 50 mm (as illustrated in said "D" configuration).

FIG. 1B is a plan view of the exemplary EP catheter 10 illustrated in FIG. 1A in an undeflected configuration (i.e., configuration "C" of FIG. 1A). FIG. 1B shows an approximate minimum length for the catheter body of on the order of about 110 cm, although other lengths can be employed according to this disclosure.

Figure 1C:
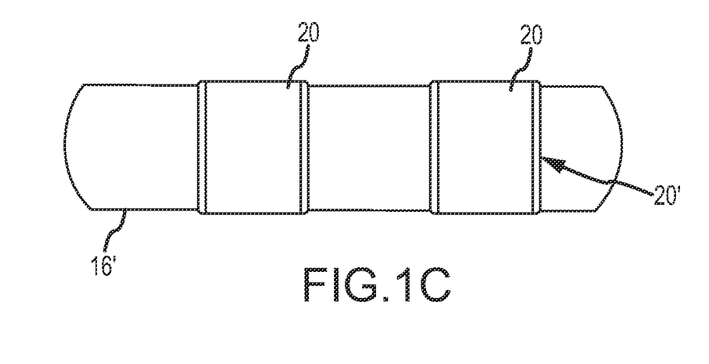
FIG. 1C is an enlarged view of the distal single shallow helical fixed-diameter loop cardiac mapping portion of the exemplary EP catheter of FIG. 1A; namely, an illustration of a pair of electrodes residing a segment of the offset shaft-to-loop axis cardiac mapping portion.

FIG. 1C is an enlarged view of the distal single shallow helical fixed-diameter loop cardiac mapping portion 16 of the exemplary EP catheter 10 of FIG. 1A; namely, an illustration of a pair of electrodes 20 residing on a segment 16' of the offset shaft-to-loop axis, single shallow helical fixed-diameter loop cardiac mapping portion 16. The lateral edges 20' of electrodes 20 are bonded to the adjacent relatively smaller (e.g., 4F) diameter biocompatible tubing (e.g., PTFE or the like) of portion 16 with a biocompatible material such as a polyurethane matrix composed of Polycin 936 and Vorite 689 (mixed 52:48 percent, as an example) produced by CasChem Inc. of Bayonne, N.J.

Figure 1D:
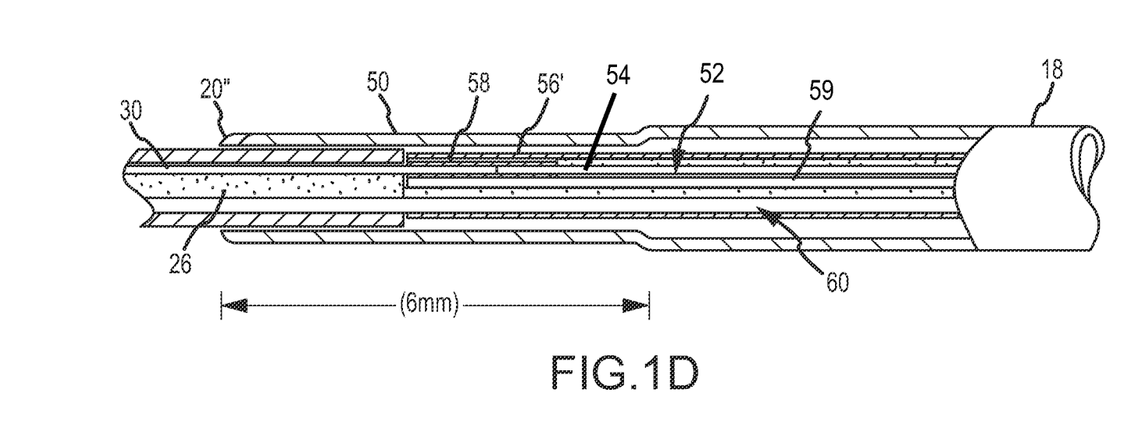
FIG. 1D is an elevational side view in partial cross section of a neck portion formed just proximal of the distal single shallow helical fixed-diameter loop cardiac mapping portion of the exemplary EP catheter depicted in FIGS. 1A and 1B.

FIG. 1D is an elevational side view in partial cross section of a neck portion 18 formed just proximal of the distal single shallow helical fixed-diameter loop cardiac mapping portion 16 of the exemplary EP catheter 10 depicted in FIGS. 1A and 1B. As shown, an extended braid tube/spring assembly 50 surrounds a variety of subcomponents of catheter 10 and is itself wrapped by a relatively smaller diameter biocompatible tubing 18 that covers the neck region and transitions the outer diameter to the about 4F distal single shallow helical fixed-diameter loop cardiac mapping portion 16. Where the extended braid tube/spring assembly 50 terminates at its distal edge a small amount of medical grade adhesive polymer 20" (e.g., like the polymer 20' used at the edges of electrodes 20) can be applied. A polyimide tube 56' passes through the assembly 50 (and neck region 18) and into the distal single shallow helical fixed-diameter loop cardiac mapping portion 16 and isolates a plurality of elongate conductive strands 70' (shown in FIG. 4B) that couple the electrodes 20, 46 to remote circuitry via a handle (22 as shown in FIGS. 1A and 1B) having a mass termination where the conductors 70 pass through the handle to couple to an EP recording system or other diagnostic equipment, for example. A flat wire subassembly 52, which includes segment of flat wire 59, is coupled to an activation wire 54 and is adapted to impart and release tension to deflect the proximal end 16 in a plane defined by the flat wire subassembly 52 (via manipulation of the handle, such as by rotation or linear actuation members, and the like). The flat wire subassembly 52 is sometimes described as a planarity member or element because it promotes such planar deflection. A short segment of polyimide tubing 56' surrounds a junction of several components; namely, a lubricous tubing member 58 (e.g., PEEK tubing) that receives a proximal end of an elongate shape memory member 30 (formed of nitinol, for example) that is preformed into a desired dimension and configuration for distal portion 16. In one embodiment, the distal portion 16 has an overall outer diameter of about 15 mm (i.e., for the outermost loop) with a 4F dimension for portion 16' and 1 mm (wide) platinum electrodes 20 and a 2 mm (long) tip electrode 46. In this embodiment, the electrodes 20 can be spaced apart in bipolar pairs or evenly (e.g., about 3 mm, 5 mm or other nominal spacing between them). In a bipolar pair configuration the electrode spacing can vary, of course, although in on embodiment the spacing for 1 mm (wide) ring-type electrodes is 1 mm per bipolar pair with 2.5 mm between pairs. In this embodiment the spacing between the tip electrode 46 to the most distal ring-type electrode 20 can be 1 mm or 2 mm or other value. In the embodiments depicted herein the diameter of the outer loop of the distal portion 16 is fixed (e.g., at about 15, mm, 20 mm or less than about 33 mm, or more, if desired). At the junction of the flat wire subassembly 52 with the nitinol wire 30 wrapped in, for example, PEEK tubing urethane adhesive (denoted by reference numeral 26 in FIG. 2B) can be applied between, above, and around the components within the polyimide tubing 56' to encapsulate same. Similarly, urethane adhesive 26 can be impregnated into the interstices of the neck region 18 and distal portion 16 to reduce or eliminate any migration of the nitinol wire 30 or PEEK tubing 58 or polyimide tube 60 (surrounding conductor 70') during use.

In general, EP catheter 10 can include an elongate catheter body 12, which, in some embodiments, is tubular (e.g., it defines at least one lumen therethrough). Catheter body 12 includes a proximal region 14, a distal portion 16, and a neck region 18 between proximal region 14 and distal portion 16. One of ordinary skill in the art will appreciate that the relative lengths of proximal region 14, distal portion 16, and neck region 18 depicted in FIGS. 1A and 1B are merely illustrative and can vary without departing from the spirit and scope of the present invention but likely should not have a magnitude of less than about 110 cm. Of course, the overall length of catheter body 12 should be long enough to reach the intended destination within the patient's body.

Catheter body 12 will typically be made of a biocompatible polymeric material, such as polytetrafluoroethylene (PTFE) tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, can be utilized. Additional suitable materials for catheter body 12 include, without limitation, polyimide-based thermoplastic elastomers (namely poly(ether-block-amide), such as PEBAX®), polyester-based thermoplastic elastomers (e.g., HYTREL®), thermoplastic polyurethanes (e.g., PELLETHANE®, ESTANE®), ionic thermoplastic elastomers, functionalized thermoplastic olefins, and any combinations thereof. In general, suitable materials for catheter body 12 can also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 12 can vary along its length. In general, the basic construction of catheter body 12 will be familiar to those of ordinary skill in the art, and thus will not be discussed in further detail herein.

Figure 2A:
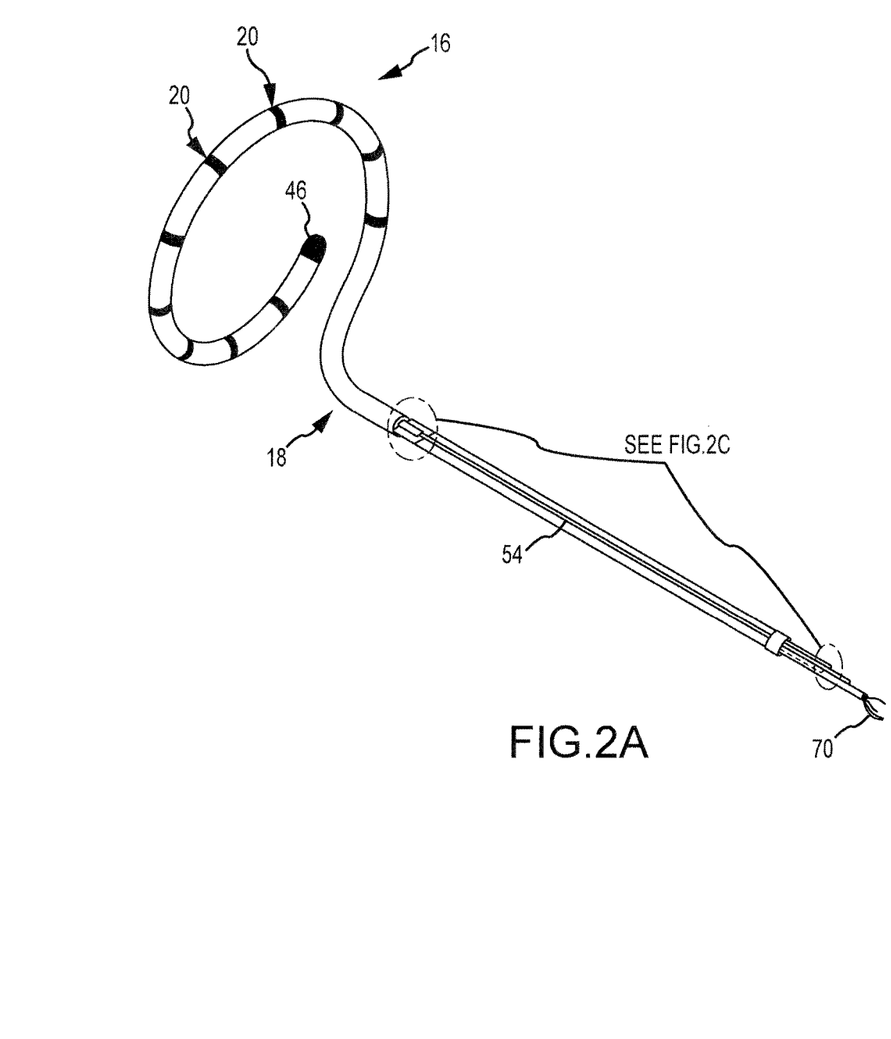
FIG. 2A is a close up isometric view of the distal single shallow helical fixed-diameter loop cardiac mapping portion of the exemplary EP catheter of FIGS. 1A and 1B (with a perspective view of connecting elements within interior portions of the catheter body, or shaft, illustrated) according to some embodiments of the present invention.

Referring now to FIG. 2A which is a close up isometric view of the distal single shallow helical fixed-diameter loop cardiac mapping portion 16 of the exemplary EP catheter 10 of FIGS. 1A and 1B (with a perspective view of connecting elements within interior portions of the catheter body, or shaft, illustrated) according to some embodiments of the present invention. As illustrated, the proximal and distal ends of the flat wire subassembly 52 (e.g., implemented to promote planarity during deflection) are emphasized.

Figure 2B:
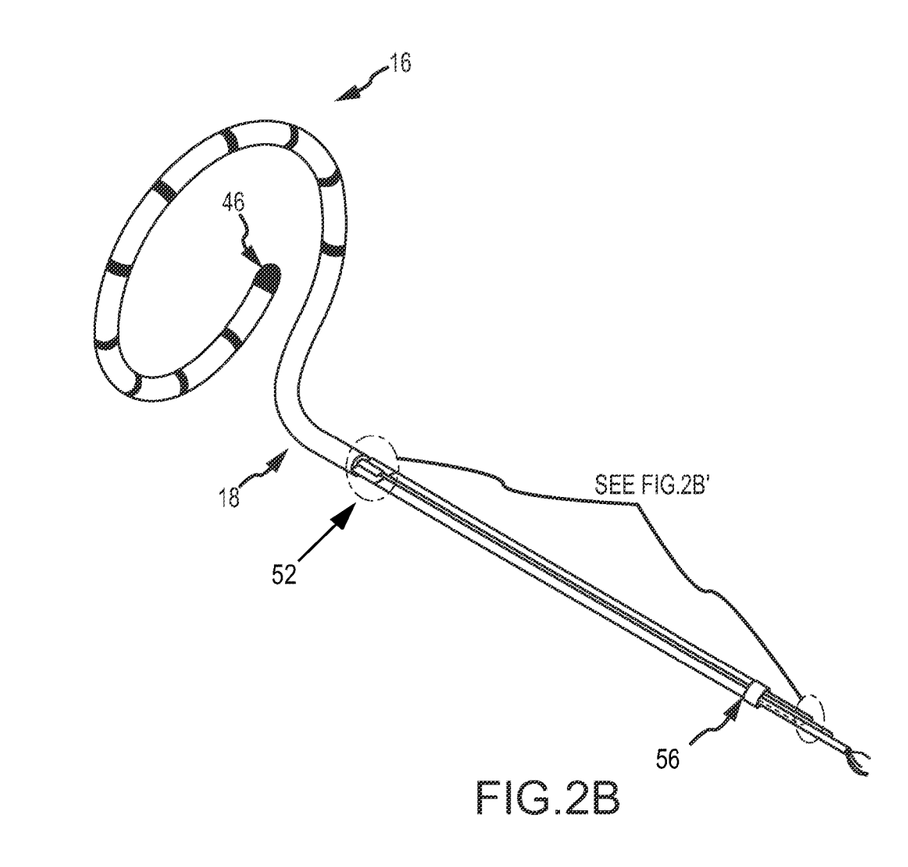
FIG. 2B is an enlarged isometric fragmented view of the interior details of the ends of the connecting elements within the interior of the catheter body shown in FIG. 2A.

FIG. 2B is an isometric illustration of the neck region 18 and the single shallow helical fixed-diameter loop distal portion 16, polyimide tubing 56, and the flat wire subassembly 52.

FIG. 2B' is an enlarged isometric fragmented view of the interior details of the ends of the various connecting elements within the interior of the catheter body 14,18 of FIG. 2A. As depicted, the proximal end of a flattened PEEK tube 58 that contains the nitinol wire 30 is adhered with urethane adhesive 26 (or other suitable medical grade adhesive) to segment of flat wire 59 of the flat wire subassembly 52 and wrapped in polyimide tubing 56' for containment. The proximal end of the flat wire subassembly 52 couples via a segment of polyimide tubing 56 filled with urethane adhesive 26 that also encapsulates the smaller diameter polyimide tubing 61 where the activation wire 54 resides. A gap of about 1-2 mm between the tubing 56 and the distal end of extended braid/spring subassembly 50 should be optionally maintained (as depicted) and the activation wire 54 and conductor wires 70 (within polyimide tube 60) are conveyed through braid/spring subassembly 50 to a handle or other remote location.

Figure 2C:
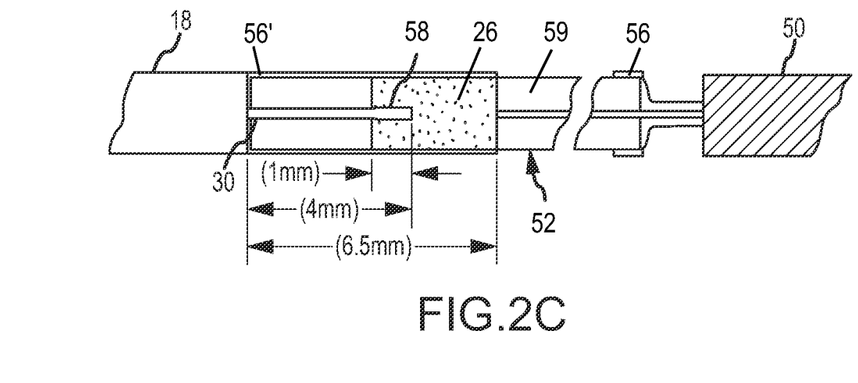
FIG. 2C is an enlarged fragmented plan view of the interior details of the ends of the connecting elements within the interior of the catheter body shown in FIG. 2A.

FIG. 2C is an enlarged fragmented plan view of the interior details of the ends of the connecting elements within the interior of the catheter body shown in FIG. 2A. As depicted, the flattened section of the PEEK tubing 58 disposed within the polyimide tubing 56' can comprise a 1 mm segment to promote adhesion to the urethane adhesive 26 impregnated therein and thus to the flat wire subassembly 52, including segment of flat wire 59. Similarly, the proximal end of the flat wire subassembly 52 can be surrounded by polyimide tubing 56 and impregnated with urethane adhesive (not shown) to promote mechanical coupling to the adjacent extended braid/spring subassembly 50. A suitable biocompatible compound 20" (e.g., such as polymer 20') can be applied to the junction between the outer covering for distal portion 16' and the neck region 18.

Figure 3:
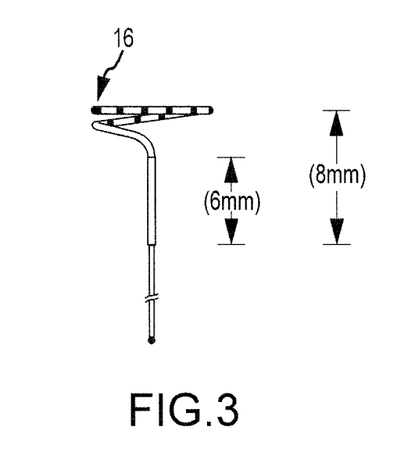
FIG. 3 is an elevational view showing exemplary dimensions of the distal single shallow helical fixed-diameter loop cardiac mapping portion of the exemplary EP catheter of FIGS. 1A and 1B according to an embodiment of the present disclosure (at the perspective illustrated the off-axis junction with the shaft is not apparent).

FIG. 3 is an elevational view showing exemplary dimensions of the distal single shallow helical fixed-diameter loop cardiac mapping portion 16 of the exemplary EP catheter 10 of FIGS. 1A and 1B according to an embodiment of the present disclosure. For example, the "plane" of the single shallow helical fixed-diameter loop distal portion 16 can be on the order of 2 mm to the neck region 18, although other dimensions can be used if desired. Whatever dimension is used the wire support length therefrom should be a reasonable length.

Figure 4A:
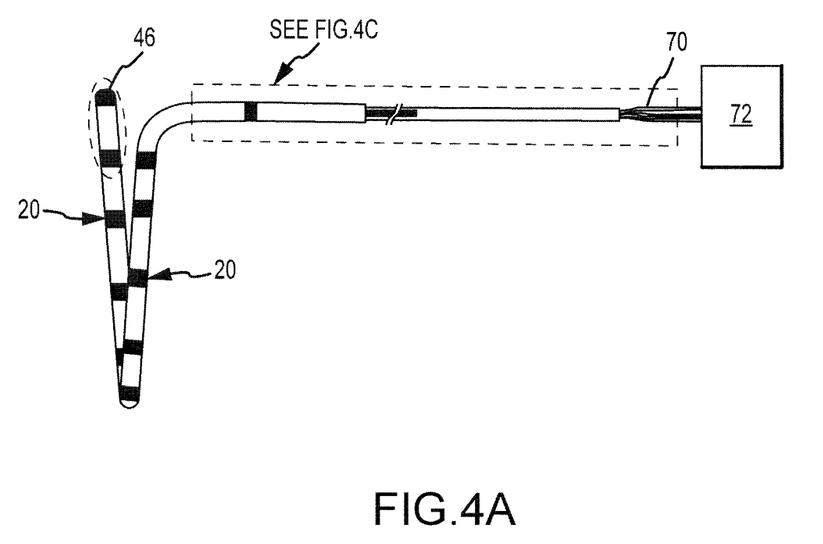
FIG. 4A depicts the distal single shallow helical fixed-diameter loop cardiac mapping portion of the exemplary EP catheter of FIGS. 1A and 1B (with cross references to details shown in FIG. 4C).
Figure 4B:
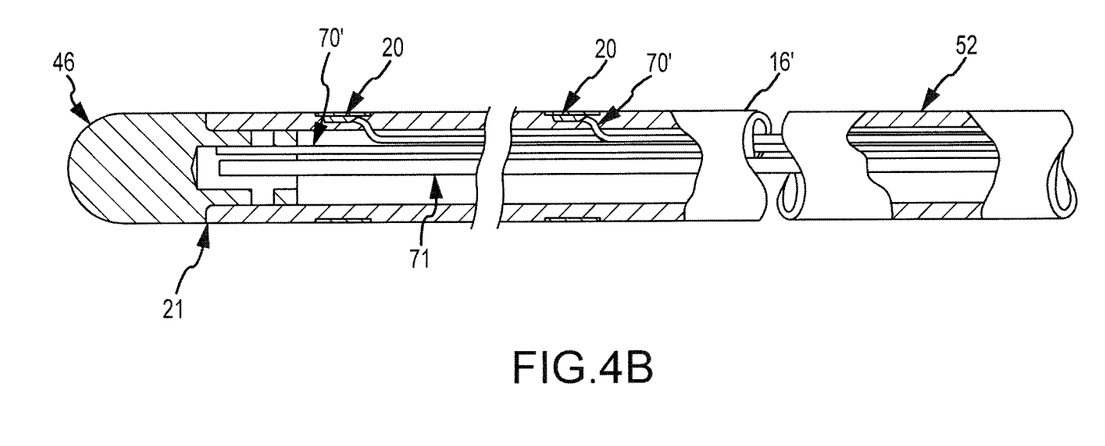
FIG. 4B is an enlarged fragmentary view in partial cross section and partial cut-away of the distal tip electrode and two ring electrodes and flat wire subassembly connection within the catheter body, respectively, shown in FIG. 4A.
Figure 4C:
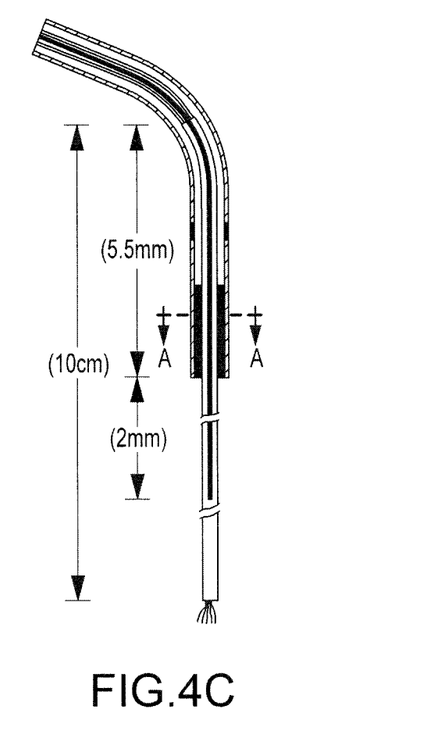
FIG. 4C is an enlarged cross sectional view of the catheter body near the neck region shown in FIG. 4A

FIG. 4A depicts the distal single shallow helical fixed-diameter loop cardiac mapping portion 16 of the exemplary EP catheter 10 of FIGS. 1A and 1B (with cross references to details shown in FIGS. 4B and 4C). In the illustrated embodiment the single shallow helical fixed-diameter loop distal portion 16 includes evenly-spaced ten-pole electrodes 20 with a nominal separation between adjacent electrodes 20. Of course, other dimensions can be used for the electrodes 20 and the spacing therebetween. At the proximal end of the catheter body 12 (not specifically shown) a plurality of individually electrically insulated elongate conductors 70 emerge and are adapted to be individually coupled to mass termination terminal 72 within a handle for ultimate electrical communication with an EP recording system, an electroanatomical localization and visualization system (e.g., such as the ENSITE system of St. Jude Medical, Inc. operating the ONEMAP facility or other similar systems for monitoring cardiac activity and providing one or more visual representations of same).

FIG. 4B is an enlarged fragmentary view in partial cross section and partial cut-away of the distal tip electrode 46 and two ring-type electrodes 20 and flat wire subassembly 52 connection within the catheter body 12, respectively, shown in FIG. 4A. Each electrode 20,46 couples via an elongate conductor 70' in FIG. 4B to remote EP recording and/or localization and visualization equipment. A biocompatible adhesive 21 (e.g., LOCTITE adhesive) can be applied to the junction of the biocompatible tubing 16 of the distal portion 16 and the electrode 46 to eliminate body fluid ingress therein. A so-called safety wire (or element) 71 can couple to the electrode 46 and a proximal location to reduce or eliminate the chance that the electrode 46 might separate from the catheter assembly 10.

FIG. 4C is an enlarged fragmentary view in partial cross section of the catheter body near the neck region shown in FIG. 4A and indicates a cross sectional view along lines A-A therein which is reflected in FIG. 5 hereinbelow described.

The dimensions indicated on FIG. 4C are merely exemplary and illustrative and not intended as limiting in any way.

Figure 5:
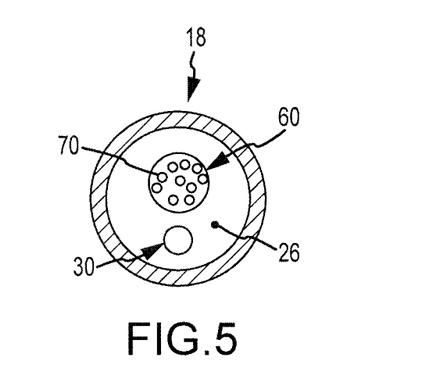
FIG. 5 is a cross-sectional view of the EP catheter illustrated in FIG. 4C taken along line A-A as shown in FIG. 4C.

FIG. 5 is a cross-sectional view of the EP catheter 10 illustrated in FIG. 4C taken along line A-A as shown in FIG. 4C. The biocompatible tubing overlaying next region 18 includes (electrode 20) conductor wires, denoted by reference numeral 70 in FIG. 5, surrounded by polyimide tubing 60 and nominally spaced from nitinol wire 30 by a space impregnated with urethane adhesive 26.

One of ordinary skill in the art will appreciate that electrodes 20 can be ring-type electrodes or any other electrodes suitable for a particular application of EP catheter 10. For example, where EP catheter 10 is intended for use in a contactless EP study, electrodes 20 can be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 20 can be employed for therapeutic purposes (e.g., cardiac ablation and/or pacing).

Referring again to the present disclosure in general, various handles and their associated actuators for use in connection with deflecting EP catheters are known, and thus handle 22 will not be described in further detail herein except that is has a means for imparting tension (e.g., push-pull knob 24 depicted in FIGS. 1A and 1B, although other biasing structures can of course be used) to an activation wire.

In use, EP catheter 10 is introduced into a patient's body proximate an area of interest, such as a pulmonary vein ostium. Of course, EP catheter can be introduced surgically (e.g., via an incision in the patient's chest) or non-surgically (e.g., navigated through the patient's vasculature to a desired site). Activation wire 54 can be actuated in order to deflect proximal region 14 of catheter body 12 such that distal portion 16 is oriented generally towards the ostium of interest. Electrodes 20 can then be employed for diagnostic or therapeutic purposes.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure can be made without departing from the invention as defined in the appended claims.

We claim:
1. An electrophysiology (EP) catheter comprising:
   a handle;
   a tubular catheter body having a proximal region coupled to a neck region which further couples to a distal portion which when in a non-compressed state is predisposed into a single shallow helical fixed-diameter loop configuration having a periphery of said loop directly coupled to the neck region at a periphery of the loop such that a central axis of the tubular catheter body is offset from a central axis of the single shallow helical fixed-diameter loop configuration;
a flat wire assembly entirely disposed between the handle and the distal portion;
an activation wire anchored to the flat wire assembly near the neck region; and
a plurality of electrodes coupled to the single shallow helical fixed-diameter loop distal portion;
wherein the distal portion has a first diameter that is less than a second diameter of the proximal region, the neck region transitioning the second diameter with the first diameter; and
wherein the catheter further comprises a braided structure embedded near a junction of the neck region adjacent the distal single shallow helical fixed-diameter loop configuration.

2. The EP catheter according to claim 1, wherein the distal single shallow helical fixed-diameter loop further includes a shape memory material comprising a nickel titanium material or an alloy thereof.

3. The EP catheter according to claim 1, wherein said plurality of electrodes includes at least two different types of electrodes, and a one electrode of said plurality of electrodes couples to a distal tip portion of the single shallow helical fixed-diameter loop configuration, and wherein a remaining group of electrodes of said plurality of electrodes is of a different type of electrode than said one of said plurality of electrodes.

4. The EP catheter according to claim 1, wherein said activation wire is conveyed through said braided structure; and wherein said handle is configured to impart tension coupled to the activation wire such that forces acting on the activation wire cause up to 180 degree deflection of the single shallow helical fixed-diameter loop relative to the tubular catheter body.

5. The EP catheter according to claim 1, wherein the handle further comprises a mass termination terminal for receiving a plurality of electrical conductors.

6. The EP catheter according to claim 3, wherein the looped region comprises at least an offset shaft-to-loop axis configuration and the plurality of electrodes comprise a plurality of discrete electrodes between about nine (9) and about nineteen (19), and a distal tip electrode, wherein said distal tip electrode is a different size than said plurality of discrete electrodes.

7. An electrophysiology (EP) catheter, comprising: an elongate catheter body including a proximal region, a distal portion, a neck region joining the distal portion to the proximal region, and wherein the distal portion is preconfigured into a single shallow helical fixed-diameter loop and wherein the neck region couples directly to a peripheral portion of said loop such that a central axis of the elongate catheter body is offset from a central axis of the single shallow helical fixed-diameter loop; a handle, said handle coupled to the proximal region of said elongate catheter body; a plurality of electrodes disposed on the distal portion, said plurality of electrodes including at least two different types of electrodes; a flat wire assembly; said flat wire assembly entirely disposed between said handle and said distal portion; an activation wire disposed within the proximal region of the catheter body and anchored to the flat wire assembly near the neck region, the activation wire operable to deflect the distal portion of the catheter body; and a shape memory structure extending through at least a portion of the distal portion and shaping the portion of the distal portion into at least a full single shallow helical fixed-diameter loop; wherein the distal portion has a first diameter that is less than a second diameter of the proximal region, the neck region transitioning the second diameter with the first diameter.

8. An EP catheter according to claim 7, wherein the neck region resides substantially along a peripheral arc defined by the single shallow helical fixed-diameter loop.

9. An EP catheter according to claim 7, wherein the shape memory structure is operable to promote a predefined radius of curvature of the single shallow helical fixed-diameter loop.

10. An EP catheter according to claim 7, wherein the handle includes an actuation mechanism operably coupled to the activation wire.

11. An EP catheter according to claim 1, further comprising an adhesive, said adhesive positioned between, above and around an end of the flat wire assembly, wherein said adhesive provides encapsulation properties.

12. An EP catheter according to claim 7, further comprising an adhesive, said adhesive positioned between, above and around an end of the flat wire assembly, wherein said adhesive provides encapsulation properties.

13. An EP catheter according to claim 1, wherein the activation wire extends from the handle and terminates within the flat wire assembly, and wherein the flat wire assembly comprises a segment of flat wire joining the activation wire and the distal portion.

14. An EP catheter according to claim 13, wherein a distal end of the activation wire is coupled to a distal region of the segment of flat wire, wherein the distal region of the segment of flat wire terminates short of the loop and any of the plurality of electrodes of the distal portion.

15. An EP catheter according to claim 13, wherein the flat wire assembly further comprises a flattened tube joining the activation wire and the segment of flat wire.

16. An EP catheter according to claim 15, wherein the flat wire assembly further comprises a tube surrounding the segment of flat wire and the flattened tube, and conductor wires extending from the handle to the plurality of electrodes through the tube.

17. An EP catheter according to claim 16, wherein the transitioning of the neck region surrounds the tube and the flattened tube.

18. An EP catheter according to claim 17, further comprising an adhesive, said adhesive positioned around the flattened tube, the conductor wires, and the segment of flat wire within the tube, wherein said adhesive provides encapsulation properties.

19. An EP catheter according to claim 15, further comprising a shape memory member extending from the flattened tube and into the dual loop of the distal looped region to provide the single shallow helical fixed-diameter loop configuration in the non-compressed state.

20. An EP catheter according to claim 1, wherein the neck region is located just proximal of the loop configuration.

* * * * *